United States Patent
Sanborn et al.

(10) Patent No.: US 9,604,951 B2
(45) Date of Patent: Mar. 28, 2017

(54) PROCESS FOR MAKING HMF FROM SUGARS WITH REDUCED BYPRODUCT FORMATION, AND IMPROVED STABILITY HMF COMPOSITIONS

(71) Applicant: ARCHER DANIELS MIDLAND COMPANY, Decatur, IL (US)

(72) Inventors: Alexandra Sanborn, Lincoln, IL (US); Erik Hagberg, Decatur, IL (US); Stephen Howard, Sherman, IL (US); Erin M Rockafellow, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/213,514

(22) Filed: Jul. 19, 2016

(65) Prior Publication Data

US 2016/0332978 A1 Nov. 17, 2016

Related U.S. Application Data

(62) Division of application No. 14/771,842, filed as application No. PCT/US2014/018186 on Feb. 25, 2014, now Pat. No. 9,422,257.

(60) Provisional application No. 61/782,539, filed on Mar. 14, 2013.

(51) Int. Cl.
*A61K 31/341* (2006.01)
*A61K 47/10* (2006.01)
*A61K 9/08* (2006.01)
*C07D 307/46* (2006.01)
*C07D 307/48* (2006.01)
*C07D 307/50* (2006.01)
*C09K 15/06* (2006.01)

(52) U.S. Cl.
CPC .............. *C07D 307/48* (2013.01); *A61K 9/08* (2013.01); *A61K 31/341* (2013.01); *A61K 47/10* (2013.01); *C07D 307/46* (2013.01); *C07D 307/50* (2013.01); *C09K 15/06* (2013.01)

(58) Field of Classification Search
CPC ........ A61K 31/341; A61K 47/10; A61K 9/08; C07D 307/46; C07D 307/48; C07D 307/50; C09K 15/06
See application file for complete search history.

(56) References Cited

U.S. PATENT DOCUMENTS 2,917,520 A * 12/1959 Cope .................... C07D 307/46
127/53

* cited by examiner

*Primary Examiner* — Erich A Leeser
(74) *Attorney, Agent, or Firm* — William B. Miller

(57) ABSTRACT

Disclosed is a process for making HMF or a derivative of HMF by dehydrating one or more hexose sugars in a reduced oxygen environment. In another, related aspect, a method for improving the stability and resistance to degradation of an HMF product involves adding one or more antioxidants to the HMF product.

2 Claims, 1 Drawing Sheet

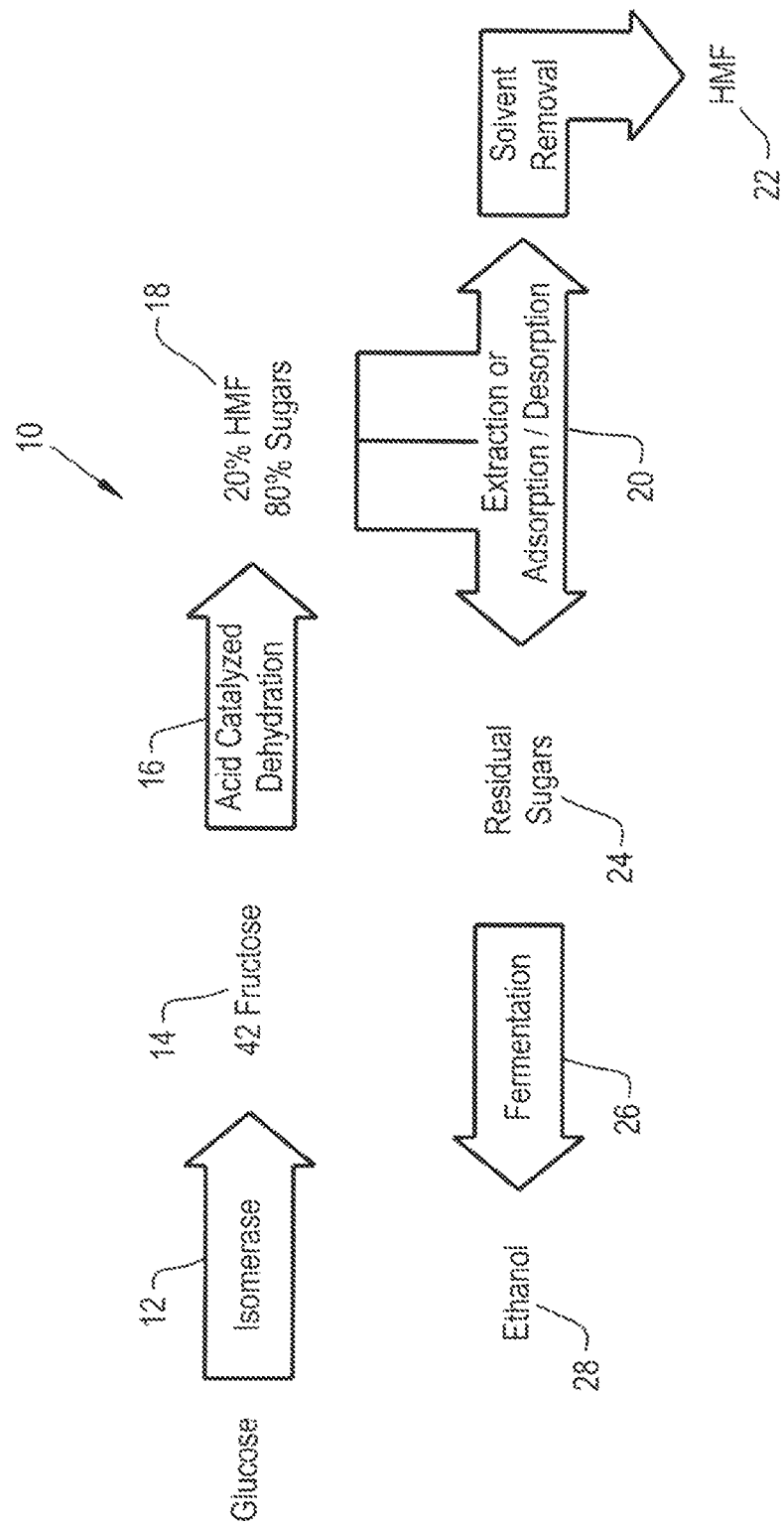

PROCESS FOR MAKING HMF FROM SUGARS WITH REDUCED BYPRODUCT FORMATION, AND IMPROVED STABILITY HMF COMPOSITIONS

CROSS-REFERENCE TO RELATED APPLICATIONS

The present application is a divisional application of U.S. Ser. No. 14/771,842, now allowed, which was filed Sep. 1, 2015 under 35 USC 371 from Patent Cooperation Treaty Application No. PCT/US2014/018186 filed Feb. 25, 2014, which in turn claimed benefit of U.S. Ser. No. 61/782,539 filed Mar. 14, 2013.

BACKGROUND

The present invention is concerned in one aspect with processes for making hydroxymethylfurfural from sugars, and particularly but without limitation, from hexose carbohydrates such as glucose and fructose. In a second aspect, the present invention relates to the hydroxymethylfurfural products produced by dehydration from such sugars.

Agricultural raw materials such as starch, cellulose, sucrose or inulin are inexpensive starting materials for the manufacture of hexoses, such as glucose and fructose. Dehydrating these hexoses produces 2-hydroxymethyl-5-furfuraldehyde, also known as hydroxymethylfurfural (HMF), among other products such as levulinic acid and formic acid. HMF and its related 2,5-disubstituted furanic derivatives have been viewed as having great potential for use in the field of intermediate chemicals from regrowing resources. More particularly, due to its various functionalities, it has been proposed that HMF could be utilized to produce a wide range of products such as polymers, solvents, surfactants, pharmaceuticals, and plant protection agents, and HMF has been reported to have antibacterial and anticorrosive properties. HMF is also a key component, as either a starting material or intermediate, in the synthesis of a wide variety of compounds, such as furfuryl dialcohols, dialdehydes, esters, ethers, halides and carboxylic acids. A notable example of a compound that can be prepared from HMF is 2,5-furandicarboxylic acid, or FDCA, which can be prepared from HMF, ether or ester derivatives of HMF through an oxidation process, see, for example, U.S. Pat. No. 7,317,116 and US 2009/0156841 to Sanborn et al. FDCA has been discussed as a biobased, renewable substitute for terephthalic acid, in the production of such multi-megaton polyester polymers as ethylene terephthalate or butylene terephthalate. FDCA esters have also recently been evaluated for replacing phthalate plasticizers for PVC, see, e.g., WO 2011/023491A1 and WO 2011/023590A1, both assigned to Evonik Oxeno GmbH, as well as R. D. Sanderson et al., Journal of Appl. Pol. Sci. 1994, vol. 53, pp. 1785-1793.

In addition, HMF has been considered as useful for the development of biofuels, fuels derived from biomass as a sustainable alternative to fossil fuels. HMF has additionally been evaluated as a treatment for sickle cell anemia. In short, HMF is an important chemical compound and a method of synthesis on a large scale to produce HMF absent significant amounts of impurities, side products and remaining starting material has been sought for nearly a century.

While it has correspondingly long been known that HMF can be prepared from sugars through dehydration, being initially prepared in 1895 from levulose by Dull (*Chem. Ztg.*, 19, 216) and from sucrose by Kiermayer (*Chem. Ztg.*, 19, 1003), chemists have differed over the years as to the precise mechanisms by which HMF is formed from certain sugars. As related very recently in Weingarten et al., "Kinetics and Reaction Engineering of Levulinic Acid Production from Aqueous Glucose Solutions", ChemSusChem 2012, vol. 5, pp. 1280-1290 (2012), "[o]verall, there are two schools of thought with regard to the mechanism of HMF formation from C6 carbohydrates. One theory postulates that the reaction proceeds by way of the acyclic 1,2-enediol intermediate. The other takes into account a fructofuranosyl cyclic intermediate in the formation of HMF from fructose." In relation to glucose, specifically, Weingarten reports that there are likewise two theories for how HMF is formed from glucose: "One theory suggests that the formation of HMF from glucose proceeds via fructose and that the near-nil presence of fructose can be attributed to its high reactivity compared to glucose. Conversely, other authors claim that glucose can be converted directly to HMF through cyclization of a 3-deoxy-glucosone intermediate formed from the open-ring form of glucose. In this respect, the relatively low conversion of glucose to HMF is caused by its low affinity to exist in the open-ring form due to stabilization of the glucose pyranose forms in aqueous solution."

While there accordingly seems to be no overriding consensus as to the precise manner in which HMF and other observed dehydration products are formed in the dehydration of hexose carbohydrates such as fructose and glucose, yet there is nevertheless a consensus that whatever mechanisms may be at work and whatever intermediate species may be formed by such mechanisms, a number of unwanted side products invariably are produced along with the HMF—whether through reactions involving the intermediate species or involving HMF—so that an economical process to make HMF on a large scale with good yields has not yet been realized. Complications arise from the rehydration of HMF, which yields by-products, such as, levulinic and formic acids. Another unwanted side reaction includes the polymerization of HMF and/or fructose resulting in humin polymers, which are solid waste products. Further complications may arise as a result of solvent selection. Water is easy to dispose of and dissolves fructose, but unfortunately, low selectivity and increased formation of polymers and humin increases under aqueous conditions.

The realization of an economical commercial production of HMF has also been hindered by HMF's comparative instability and tendency to degrade, so that purification of the HMF from the various side products and from unconverted sugars has itself proved difficult. On long exposure to temperatures at which the desired product can be distilled, for example, HMF and impurities associated with the synthetic mixture tend to form tarry degradation products. Because of this heat instability, a falling film vacuum still must be used. Even in such an apparatus, resinous solids form on the heating surface causing a stalling in the rotor and frequent shut down time making the operation inefficient. Prior work has been performed with distillation and the addition of a non-volatile solvent like PEG-600 to prevent the buildup of solid humin polymers (Cope, U.S. Pat. No. 2,917,520). Unfortunately, the use of polyglycols leads to the formation of HMF-PEG ethers.

Still other more recent efforts to deal with HMF's comparative instability and tendency to degrade have sought to either form more stable and easily separated HMF derivatives, for example, HMF ester and ether derivatives, or to quickly remove the HMF from exposure to those conditions, for example, acidic conditions, tending to contribute to its degradation.

An example of the former approach may be found in the previously-cited US 2009/0156841 by Sanborn et al., in which a method is provided of producing substantially pure HMF and HMF esters from a carbohydrate source by contacting the carbohydrate source with a solid phase catalyst; "substantially pure" was defined as referencing a purity of HMF of about 70% or greater, optionally about 80% or greater, or about 90% or greater.

A method of producing HMF esters from a carbohydrate source and organic acids involved, in one embodiment, heating a carbohydrate starting material with a solvent in a column, and continuously flowing the heated carbohydrate and solvent through a solid phase catalyst in the presence of an organic acid to form a HMF ester. The solvent is removed by rotary evaporation to provide a substantially pure HMF ester. In another embodiment, a carbohydrate is heated with the organic acid and a solid catalyst in a solution to form an HMF ester. The resulting HMF ester may then be purified by filtration, evaporation, extraction, and distillation or any combination thereof.

An example of the latter approach may be found in WO 2009/012445 by Dignan et al., wherein HMF is proposed to be made by mixing or agitating an aqueous solution of fructose and inorganic acid catalyst with a water immiscible organic solvent to form an emulsion of the aqueous and organic phases, then heating the emulsion in a flow-through reactor at elevated pressures and allowing the aqueous and organic phases to phase separate. HMF is present in the aqueous and organic phases in about equal amounts, and is removed from both, for example, by vacuum evaporation and vacuum distillation from the organic phase and by passing the aqueous phase through an ion-exchange resin. Residual fructose stays with the aqueous phase. High fructose levels are advocated for the initial aqueous phase, to use relatively smaller amounts of solvent in relation to the amount of fructose reacted.

In WO 2013/106136 to Sanborn et al., we described a new process for making HMF or HMF derivatives (e.g., the ester or ether derivatives) from an aqueous hexose sugar solution in which, according to certain embodiments, the acid-catalyzed dehydration step is conducted with rapid heating of the aqueous hexose solution from an ambient to a reaction temperature, as well as with rapid cooling of the HMF and/or HMF derivative unconverted sugar mixture prior to the separation of the fermentation-ready residual sugars product from the HMF and/or HMF derivative product. In addition, the time between when the aqueous hexose solution has been introduced into a reactor and the HMF and/or HMF ether products begin to be cooled is preferably limited.

By accepting limited per-pass conversion to HMF, the overall exposure of the HMF that is formed from any given aqueous hexose solution to acidic, elevated temperature conditions is limited, and preferably little to no unwanted or unusable byproducts such as humins are produced requiring waste treatments. Separation and recovery of the products is simplified and levels of HMF and other hexose dehydration products known to inhibit ethanol production by fermentation are reduced in the residual sugars product to an extent whereby the residual sugars product can be used directly for ethanol fermentation if desired. Processes conducted as described were characterized by very high sugar accountabilities and high conversion efficiencies, with very low losses of sugars being apparent.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this understanding, in one aspect, the invention concerns a still different approach to resolving some of the difficulties that have been encountered in seeking to manufacture HMF on a commercial scale, especially from common hexose sugars from corn wet or dry milling or from the cellulosic fraction of a lignocellulosic biomass, for example, through providing a process for making HMF or a derivative of HMF by dehydrating one or more hexose sugars in a reduced oxygen environment.

In another, related aspect, the present invention concerns a method for improving the stability and resistance to degradation of an HMF product such as may be produced from the acid dehydration of one or more hexose sugars, through combination of the HMF product with one or more antioxidants, where "antioxidants" is understood to refer broadly to those compounds and combinations of compounds which are directly or indirectly capable of limiting or even preventing, regardless of a particular mode of action, the complex phenomena of oxidation, including autooxidation, of organic substances of natural or synthetic origin, of a monomeric or polymeric nature, and further concerns the improved stability HMF compositions themselves including one or more antioxidants. Thus, for example, "antioxidants" as used herein will be understood to include those materials which have been conventionally described as antioxidants per se, as well as materials which have been conventionally described or categorized differently, e.g., oxygen scavengers.

In still a further aspect, the invention concerns a method for improving the stability and resistance to degradation of a stored HMF product such as may be produced from the acid dehydration of one or more hexose sugars prior to its use, comprising storing the HMF product in a reduced oxygen environment.

BRIEF DESCRIPTION OF THE DRAWING

FIG. 1 is a schematic representation of a process according to the present invention in one illustrative embodiment.

DETAILED DESCRIPTION OF ILLUSTRATIVE EMBODIMENTS

The comparative instability and tendency to degrade of HMF has already been noted. The exposure of HMF to acidic, elevated temperature conditions has been known to contribute to the degradation of HMF, but the present invention is based upon the discovery that oxidation, including especially auto-oxidation, of HMF also plays a heretofore unappreciated role. By conducting a dehydration of one or more hexose sugars in a reduced oxygen environment, and/or by combining HMF with one or more antioxidants, significant improvements in the stability and resistance to degradation of the HMF can be realized.

While those skilled in the art will readily appreciate that the nature of the invention is such as permits its practical utilization with any known method of dehydrating one or more hexoses to form HMF or to form a derivative of HMF as desired, nevertheless for purposes of illustration only, one embodiment 10 of a process of the present invention is shown schematically in FIG. 1. In particular, embodiment 10 concerns a modified process otherwise according to the above-mentioned WO 2013/106136 to Sanborn et al., wherein the dehydration is carried out in a reduced oxygen environment and/or wherein one or more antioxidants are combined with the HMF and/or HMF derivatives made according to a process carried out as described in that application, or carried out as described therein but in a reduced oxygen environment for the dehydration step.

Turning now to FIG. 1, the aqueous hexose solution that is dehydrated to make HMF or an HMF derivative can generally comprise one or more of the six-carbon sugars (hexoses). In particular embodiments, the aqueous hexose solution can comprise one or both of the more common hexoses glucose and fructose and in certain embodiments will comprise both of glucose and fructose. The embodiment 10 schematically shown in FIG. 1 is based on an aqueous hexose solution including both of glucose and fructose.

In the process 10, glucose as may be derived from the hydrolysis of starch with acids or enzymes or from the hydrolysis of cellulosic materials is first enzymatically converted in step 12 through use of an isomerase to a mixture of glucose and fructose, in the form of aqueous hexose sugar solution 14. Processes for making glucose from starch and for converting a portion of the glucose to fructose are well known, for example, in the making of high fructose corn syrups. Alternatively, of course, fructose derived from cane sugar or sugar beets, rather than from an isomerization of glucose, may be combined with glucose in a desired proportion. In still another embodiment, a combination of isomerization of glucose plus blending in of fructose from other known sources may be employed, to provide a combination of glucose and fructose for forming an aqueous hexose sugar solution for further processing. Conveniently, the aqueous hexose sugar solution 14 can correspond to a current high fructose corn syrup product, for example, HFCS 42 (containing about 42 percent fructose and about 53 percent glucose), HFCS 90 (made from HFCS 42 by additional purification, about 90 percent fructose and about 5 percent each of glucose and maltose) or HFCS 55 (containing about 55 percent fructose, conventionally made from blending HFCS 42 and HFCS 90), so that existing HFCS production capacity can be utilized to make HMF and derivative products to improve asset utilization and improve returns on capital, as HFCS demand and pricing and HMF and HMF derivative demand and pricing would indicate.

The aqueous hexose sugar solution 14 then undergoes an acid-catalyzed dehydration in step 16, to provide a mixture 18 of HMF and unconverted sugars. Because fructose dehydrates much more readily than glucose, the proportion of glucose in the unconverted sugars of mixture 18 will be higher than in the hexose sugar solution 14. The relative amounts of HMF and of the unconverted hexose sugars in the mixture 18, and the relative amounts of glucose and fructose in the unconverted sugars portion, can vary dependent on the manner in which the acid dehydration step 16 is conducted as well as on the composition of the aqueous hexose sugar solution 14. In general, of course, where HMF production is to be favored over the production of ethanol from the unconverted, residual sugars, HFCS 90 will produce more HMF given the same acid dehydration conditions than will HFCS 55, and HFCS 55 will produce more than HFCS 42 (since fructose more readily dehydrates to HMF than does glucose).

In certain embodiments, as mentioned above, the acid-catalyzed dehydration step 16 is conducted with rapid heating of the aqueous hexose sugar solution 14 from an ambient temperature to the desired dehydration reaction temperature, and then with rapid cooling of the HMF/unconverted sugar mixture 18 prior to the separation of the fermentation-ready residual sugars product from the HMF product. As well, the time from the introduction of sugar solution 14 until HMF/unconverted sugar mixture begins to be cooled is also limited.

By accepting limited per-pass conversion to HMF in this fashion, the overall exposure of the HMF that is formed to acidic, elevated temperature conditions is correspondingly limited, so that preferably little to no unwanted or unusable byproducts such as humins are produced requiring waste treatments. Separation and recovery of the products is simplified and levels of HMF and other hexose dehydration products known to inhibit ethanol production by fermentation are reduced in the residual sugars product to an extent whereby the residual sugars product can be used directly for ethanol fermentation if desired.

Consequently, typically the mixture 18 will comprise from 10 to 55 percent molar yield of HMF, from 30 to 80 percent molar yield of unconverted, residual sugars, and not more than 10 percent molar yield of other materials such as furfural, levulinic acid, humins etc. Preferably, the mixture 18 will comprise from 30 to 55 percent yield of HMF, from 40 to 70 percent yield of unconverted, residual sugars, and not more than 5 percent yield of other materials such as furfural, levulinic acid, humins etc. More preferably, the mixture 18 will comprise from 45 to 55 percent yield of HMF, from 25 to 40 percent yield of unconverted, residual sugars, and not more than 5 percent yield of other materials such as furfural, levulinic acid, humins etc.

In addition to seeking to limit the overall exposure of the HMF that is formed to acidic, elevated temperature conditions, in the illustrative embodiment 10 of a dehydration process according to the present invention, the acid-catalyzed dehydration step 16 is conducted in a reduced oxygen environment wherein a sub-atmospheric oxygen content prevails. The oxygen is preferably displaced by an inert gas, for example, nitrogen or argon. Preferably, a reduced oxygen environment is established within the reactor space prior to introducing the aqueous hexose sugar solution 14, or at least prior to any exposure of the aqueous hexose sugar solution 14 to an acid catalyst for carrying out the dehydration step 16.

Returning now to FIG. 1, the HMF and unconverted, residual sugars in mixture 18 are then separated by adsorption, solvent extraction, or a combination of these in separation step 20, to yield an HMF product stream or portion 22 and a fermentation-ready sugars stream or portion 24 which can optionally be supplied to an ethanol fermentation step 26 for producing an ethanol product 28.

Adsorption in step 20 can be by means of any material which preferentially adsorbs HMF from the residual hexose sugars in the mixture 18. A material which has been found to be very effective at retaining the HMF and any levulinic acid formed in the acid-catalyzed dehydration step 16 is DOWEX® OPTIPORE® V-493 macroporous styrene-divinylbenzene resin (CAS 69011-14-9, The Dow Chemical Company, Midland, Mich.), which has been described by its manufacturer as having a 20-50 mesh particle size, a 46 angstrom mean pore size and 1.16 mL/g pore volume, a surface area of 1100 sq. meters/g and a bulk density of 680 g/liter. An ethanol wash was effective for desorbing most of the adsorbed HMF, and subsequent washing of the resin with acetone provided quantitative recovery of the HMF that was adsorbed. An alternative is AMBERLITE™ XAD™-4 polystyrene divinylbenzene polymeric adsorbent resin (CAS 37380-42-0, Rohm & Haas Company, Philadelphia, Pa.), a non-functionalized resin having a 1.08 g/mL dry density, a surface area of 725 square meters per gram, an average pore diameter of 50 angstroms, a wet mesh size of 20-60 and a pore volume of 0.98 m L/gram. Other suitable adsorbents can be activated carbon, zeolites, alumina, clays, non-functionalized resins (LEWATIT® AF-5, LEWATIT® S7968, LEWATIT® VPOC1064 resins, all from Lanxess AG), Amberlite® XAD-4 macroreticular crosslinked polystryrene divinylbenzene polymer resin (CAS 37380-42-0, Rohm & Haas Company, Philadelphia, Pa.), and cation exchange resins, see U.S. Pat. No. 7,317,116 (Sanborn) and the later U.S. Pat. No. 7,897,794 (Geier and Soper). Desorption solvents may include polar organic solvents, for example, alcohols such as ethanol, amyl alcohol, butanol and isopentyl alcohol, as well as ethyl acetate, methyl tetrahydrofuran and tetrahydrofuran.

Suitable solvents for solvent extraction include methyl ethyl ketone and especially ethyl acetate, due to the latter's great affinity for HMF and levulinic acid, low boiling point (77 deg. C) and ease of separation from water. As demonstrated in certain of the examples of the WO 2013/106136 application, virtually complete recovery of the sugars and of the HMF from mixture 18 can be accomplished through a series of ethyl acetate extractions. Additionally, while the residual sugars recovered by other means were still suitable for being directly processed to ethanol in the subsequent ethanol fermentation step 26, those recovered following the quantitative extraction with ethyl acetate were observed to be significantly less inhibitory even under non-optimal conditions. A variety of other solvents have been suggested or used in the literature related to HMF and HMF derivative synthesis and recovery in biphasic systems, and these may be appropriate for use in the context of the present invention. Examples of other useful solvents are butanol, isoamyl alcohol, methyl ethyl ketone, methyl isobutyl ketone, diethyl ether, cyclopentyl dimethyl ether, methyl tetrahydrofuran, and methyl butyl ether.

Ethanol fermentation step 26 can encompass any known process whereby a hexose sugars feed of the type represented by fermentation-ready sugars stream or portion 24 may be converted to one or more products inclusive of ethanol, at least in some part by fermentation means. Both aerobic and anaerobic processes are thus contemplated, using any of the variety of yeasts (e.g., *kluyveromyces lactis, kluyveromyces lipolytica, saccharomyces cerevisiae, s. uvarum, s. monacensis, s. pastorianus, s. bayanus, s. ellipsoidues, candida shehata, c. melibiosica, c. intermedia*) or any of the variety of bacteria (e.g., *clostridium sporogenes, c. indolis, c. sphenoides, c. sordelli, candida bracarensis, candida dubliniensis, zymomonas mobilis, z. pomaceas*) that have ethanol-producing capability from the fermentation-ready sugars stream or portion 24 under aerobic or anaerobic conditions and other appropriate conditions. The particular yeasts (or bacteria) used and other particulars of the fermentations employing these various yeasts (or bacteria) are a matter for routine selection by those skilled in the fermentation art, though the examples below demonstrate the functionality of one common anaerobic yeast strain, *saccharomyces cerevisiae*. Given that the sugars stream or portion 24 derives from a process for making the acid dehydration product HMF, a yeast or bacteria that has been demonstrated for use particularly with sugars derived from a lignocellulosic biomass through acid-hydrolyzing the biomass and/or a cellulosic fraction from biomass may be preferred. For example, the aerobic bacterium *corynebacterium glutamicum* R was evaluated in Sakai et al., "Effect of Lignocellulose-Derived Inhibitors on Growth of and Ethanol Production by Growth-Arrested *Corynebacterium glutamicum* R", Applied and Environmental Biology, vol. 73, no. 7, pp 2349-2353 (April 2007), as an alternative to detoxification measures against organic acids, furans and phenols byproducts from the dilute acid pretreatment of biomass, and found promising.

While the amounts of HMF (and/or HMF ethers, as the case may be) and of unconverted, residual sugars may vary somewhat, preferably in all embodiments a high degree of sugar accountability is achieved, where "sugar accountability" is understood to refer to the percentage of sugars input to the acid dehydration step 16 that can be accounted for in adding the molar yields of identifiable products in the mixture 18—essentially adding the molar yields of HMF (and/or of HMF ethers), levulinic acid, furfural and residual, unconverted sugars. Preferably, a modified process 10 according to the present invention is characterized by a total sugar accountability of at least 70 percent, more preferably at least 80 percent and most preferably at least 90 percent.

The fermentation-ready sugars stream or portion 24 can, in whole or in part, also be used for other purposes beyond the production of ethanol. For example, sugars in stream or portion 24 can be recycled to the beginning of the acid dehydration step 16 for producing additional HMF or HMF ethers. The hexose sugars represented by stream or portion 24 can also be hydrogenated to sugar alcohols for producing other biobased fuels and fuel additives (other than or in addition to ethanol), see, for example, U.S. Pat. No. 7,678,950 to Yao et al. The sugars in stream or portion 24 can be fermented to produce lysine or lactic acid according to known methods, or used for making another dehydration product such as levulinic acid. Still other uses will be evident to those skilled in the art, given the character of the sugars stream or portion 24 provided by the described process.

A number of prospective uses of HMF product stream or portion 22 have already been mentioned, but one important contemplated use would be in the manufacture of 2,5-furandicarboxylic acid (FDCA) using a Mid-Century type Co/Mn/Br oxidation catalyst under oxidation conditions, as described in United States Pat. Application Publication No. US 2009/1056841 to Sanborn et al. and in Patent Cooperation Treaty Application Ser. No. PCT/US12/52641, filed Aug. 28, 2012 for "Process for Producing Both Biobased Succinic Acid and 2,5-Furandicarboxylic Acid", now published as WO 2013/033081. Where the HMF product stream or portion 22 is not directly used in a transformative process or otherwise may be exposed to an oxygen source in use such that an undesirable degradation of the HMF (or of an HMF derivative which is susceptible of degrading, albeit to a lesser extent) through autooxidation is foreseeable (processes for carrying out an oxidation of the HMF product stream or portion 22 or of some portion thereof to produce, e.g., FDCA, being examples of transformative processes involving the purposeful interaction of oxygen with HMF), preferably one or more antioxidants are combined with the HMF product stream or portion 22 or with some portion thereof that is foreseeably exposed to an oxygen source and at risk of degrading through autooxidation.

While the examples below utilize butylated hydroxyanisole (BHA) as the antioxidant additive, those skilled in the art will appreciate that a number of materials are well-known and used as antioxidants or as oxygen scavengers in other contexts of use, and it will be well within the capabilities of those skilled in the art to select materials (or combinations of materials) other than BHA which could be used in the process of the present invention, and to determine the amounts needed of such materials to improve the stability and resistance to degradation of HMF or of an HMF derivative that is otherwise susceptible to degrading through autooxidation. Given the substantial interest, as mentioned previously, in FDCA and FDCA esters for various polymer applications, those materials which have previously been found well-suited for use as antioxidants in polymer compositions are expected to find wider use commercially in the practice of the present invention. Various such materials may be found in, for example, chapter 1, entitled "Antioxidants", of the *Plastics Additive Handbook,* 5th ed., Carl Hanser Verlag, Munich, Germany (2001).

As previously indicated, the acid dehydration step 16 is preferably conducted in a manner to limit per-pass conversion to HMF and the exposure of the HMF that is formed to acidic, elevated temperature conditions. Rapid heating of the hexose sugar solution 14, as well as rapid cooling of the HMF/unconverted sugar mixture produced from the acid dehydration step 16, are desirable for accomplishing these objectives for a given amount of hexose sugar solution 14. Further, once the aqueous hexose solution 14 has reached the desired reaction temperature range, the extent to which the aqueous hexose solution remains subject to the acidic, elevated temperature conditions is preferably also limited. While optimal conditions will vary somewhat from one embodiment to the next, for example, in processing HFCS 42 versus HFCS 55 versus HFCS 90 as shown clearly in the WO 708 application, in general terms for a concentrated sulfuric acid content of about 0.5 percent by weight based on the mass of hexose sugars in the sugar solution 14 (or the equivalent acid strength, for other acid catalysts), a reaction temperature of from 175 degrees Celsius to 205 degrees Celsius, a dry solids loading of sugars in the range of from 10 to 50 percent, a final dry solids concentration of from 10 to 25 percent, and an average residence or reaction time of from 2 to 10 minutes appear to be advantageous. "Average residence or reaction time" or similar terminology as used herein refers to the time elapsed from the introduction of the sugar solution 14 into a reactor until cooling of the mixture 18 is commenced.

As a general matter, of course, it would be preferable to process sugar solutions 14 having a greater loading of the hexose sugars rather than a lesser loading, though some trade-offs were observed in terms of overall sugars accountability and in other respects, and these would need to be considered in determining the optimum conditions to be observed for a given feedstock. Similarly, milder reaction conditions generally provide lesser conversion, but enable increased sugars accountability.

For the particular example of a 40 percent dry solids loading HFCS 42 feed providing up to a 20 percent final dry solids concentration, using a shorter reaction time and a temperature toward the higher end seem preferable, for example, 5 minutes at 200 degrees Celsius. For HFCS 90, given the same acid starting concentration, the reaction temperature can be in the range of from 185 degrees to 205 degrees Celsius, the dry solids loading of hexose sugars in the sugar solution 14 can be from 30 to 50 percent and provide an 8 to 15 percent final dry solids concentration, and a reaction time can be from 5 to 10 minutes.

As an illustration of the considerations involved in processing one feedstock versus another, for HFCS 90 in contrast to HFCS 42, a final dry solids concentration of 20 percent could not be processed with the same overall sugars accountability, and a lower final dry solids concentration was indicated as preferable. For a final dry solids concentration of 10 percent, a reaction temperature of 185 degrees Celsius and a reaction time of 10 minutes were observed to provide favorable results. Favored conditions for the recovered sugars in stream or portion 24, it should be noted, may differ from those contemplated for freshly-supplied sugars in sugar solution 14 where recycle is contemplated for making additional HMF product.

In any event, the heating to the desired reaction temperature is preferably accomplished in not more than 15 minutes, preferably is accomplished in 11 minutes of less, more preferably in not more than 8 minutes and still more preferably is accomplished in not more than five minutes. As demonstrated by the examples of the WO 2013/106136 application, rapid feeding of a quantity of ambient hexose sugar solution to a hot aqueous acid matrix (in two minutes) gave consistent improvements in one or more of HMF selectivity, yield and overall sugar accountability compared to less rapid feeding, even given the same elapsed time between when the quantity of hexose sugar solution was fully introduced and when cooling was initiated. Rapid cooling from the reaction temperature to 50 degrees Celsius and lower is preferably accomplished in not more than 5 minutes, especially 3 minutes or less.

More particularly, in a batch reactor combining the sugar solution 14 and the acid catalyst in a hot reactor already close to or at the desired reaction temperature provides improved results as compared to where the sugar solution 14 and acid catalyst are added to a reactor and then heated gradually together to the desired reaction temperature.

In regard to continuous processes, one suitable means for rapidly heating the sugar solution 14 and the acid catalyst would be direct steam injection. A commercially-available, in-line direct steam injection device, the Hydro-Thermal Hydroheater™ from Hydro-Thermal Corporation, 400 Pilot Court, Waukesha, Wis., injects sonic velocity steam into a thin layer of a liquid (such as the sugar solution 14) flowing from an inlet pipe through a series of gaps. Steam flow is adjusted precisely through a variable area nozzle to an extent whereby outlet fluid temperatures are claimed to be controllable within 0.5 degrees Fahrenheit over a large liquid turndown ratio. Turbulent mixing takes place in a specifically designed combining tube, with an adjustable degree of shear responsive to adjustments of the steam flow and the liquid flow through (or pressure drop across) the series of gaps. Devices of this general character are described in, for example, U.S. Pat. No. 5,622,655; U.S. Pat. No. 5,842,497; U.S. Pat. No. 6,082,712; and U.S. Pat. No. 7,152,851.

In the examples reported in WO 2013/106136 using such a device, the highest HMF yield and sugar accountability from HFCS 42 syrup included a system of sulfuric acid (0.5% by wt of sugars), an initial dry solids concentration of 20% and rapid heating of the reaction mixture by direct steam injection with a system back pressure of 1.48 MPa, gauge to 1.52 MPa, gauge (215-220 psig), a steam pressure of 1.9 MPa, gauge (275 psig), a time of 5-6 minutes at the reaction temperatures provided by the direct steam injection and rapid cooling of the product mixture before pressure relief. The reaction control set point, as monitored by the temperature control element, was 200 degrees Celsius and the maximum temperature achieved at the end of the resting tube was 166 degrees Celsius. HMF was obtained with these conditions in up to 20% molar yield with greater than 90% total sugar accountability. There was virtually no visible production of insoluble humins.

For HFCS 90 syrup processed in the same apparatus, the highest HMF yield and sugar accountability included a system of sulfuric acid (0.5% by wt of sugars) an initial dry solids concentration of 10% and rapid heating of the reaction mixture by direct steam injection with a system back pressure of 1 MPa, gauge (150 psig), a steam pressure of 1.4 MPa, gauge (200 psig), a time of 11 minutes at the reaction temperatures provided by the direct steam injection and rapid cooling of the product mixture before pressure relief. The reaction control set point was 185 degrees C. and the maximum temperature achieved at the end of the resting tube was 179 degrees C. HMF was obtained from HFCS 90 with these conditions up to 31% molar yield with greater than 95% total sugar accountability. There was again virtually no visible production of insoluble humins.

Rapid cooling of the mixture 18 can be accomplished by various means. For example, while a brazed plate heat exchanger was used in at least certain of the examples below prior to a pressure reduction, other types of exchangers could be used. Other options will be evident to those of routine skill in the art It will be appreciated that the acid-catalyzed dehydration step 16 can be conducted in a batchwise, semi-batch or continuous mode. A variety of acid catalysts have been described previously for the dehydration of hexose-containing materials to HMF, including both homogeneous and heterogeneous, solid acid catalysts. Solid acid catalysts would be preferred given they are more readily separated and recovered for reuse, but selecting a catalyst that will maintain a satisfactory activity and stability in the presence of water and at the temperatures required for carrying out the dehydration step 16 can be problematic. Sulfuric acid was used in the examples of the WO 2013/106136 application and is used in the examples below, and provided good yields and excellent sugar accountabilities.

The present invention is illustrated by the following examples:

Example 1 and Comparative Example 1

Crystalline fructose (5 g) was dissolved in 7 mL of water, and charged to a two neck 25 mL round bottom flask. The flask was equipped with a tube to sparge gas (either dry air (Comp. Ex. 1) or nitrogen (Ex. 1)) through the solution and with a reflux condenser. The gas (dry air or nitrogen) was sparged through the solution for five minutes, then one drop of concentrated sulfuric acid was added to the solution. The flask was then closed with rubber septa, inserting a 16 gauge needle to allow sparge gas to escape, and refluxed for 7 hours. After 7 hours' reaction time, the contents from both of the dry air-sparged and nitrogen-sparged runs were amber in color, but from proton NMR the reactor contents of the nitrogen-sparged run were substantially free of levulinic and formic acids (Table 1), while the conventional dry air-sparged reactor contents showed significant amounts of both.

TABLE 1

| Sparge Gas | Fructose Conversion (%) | HMF (%) | Levulinic Acid (%) | Formic Acid (%) |
| --- | --- | --- | --- | --- |
| Nitrogen | 3.17 | 2.99 | ND | 0.18 |
| Dry air | 5.8 | 4.91 | 0.93 | 1.57 |

Examples 2-5 with Comparative Examples 2-5

To a vial containing 500 mg of melted hydroxymethylfurfural was 1000 ppm by weight of butylated hydroxyanisole (BHA) (Ex. 2). The mixture was vortex stirred, then placed in an oven set to 85 degrees Celsius. For comparison, a vial containing 500 mg of melted hydroxymethylfurfural but no BHA (Comp. Ex. 2) was placed in the oven alongside the first vial.

A second set of samples—Example 3 and Comparative Example 3—were prepared by combining 850 mg of HMF with 150 mg of water; to one of the samples was added 1000 ppm equivalent of BHA, while nothing was added to the second. Both samples were vigorously stirred and placed in an 85 deg. C oven.

Four samples of 10 percent by weight of HMF in water were then prepared by combining 100 mg of HMF with 900 mg of water. To one of the samples (Ex. 4) was added 1000 ppm equivalent of BHA. For a second sample (Ex. 5), the air was purged by bubbling argon through the solution and the vial was sealed to preserve the HMF under an argon atmosphere. For the third sample (Comp. Ex. 4), 10% formic acid by mass of HMF was spiked into the vial. The fourth sample (Comp. Ex. 5) was not modified at all. All four samples were again placed in the 85 degrees Celsius oven after vigorous stirring.

The compositions of the various vials were analyzed after 1 week and then again after 2 weeks (with the exception of the argon-sparged sample), with the results shown in Tables 2 and 3, respectively:

TABLE 2

One Week

| Example | Description | HMF (wt. %) | Formic (wt. %) | Levulinic (wt. %) |
| --- | --- | --- | --- | --- |
| Ex. 2 | HMF w/BHA | 87.26 | 0.12 | 0.32 |
| Comp. Ex. 2 | HMF | 82.27 | 0.35 | 0.38 |
| Ex. 3 | 85% HMF w/BHA | 81.86 | 0.10 | 0.04 |
| Comp. Ex. 3 | 85% HMF | 79.51 | 0.28 | 0.43 |
| Ex. 4 | 10% HMF w/BHA | 8.41 | 0.15 | 0.12 |
| Comp. Ex. 4 | 10% HMF w/formic | 8.49 | 0.24 | 0.30 |
| Ex. 5 | 10% HMF w/Ar | 9.17 | 0.12 | 0.04 |
| Comp. Ex. 5 | 10% HMF | 8.47 | 0.15 | 0.13 |

TABLE 3

Two Weeks

| Example | Description | HMF (wt. %) | Formic (g/L) | Levulinic (g/L) |
| --- | --- | --- | --- | --- |
| Ex. 2 | HMF w/BHA | 85.61 | 2.82 | 2.25 |
| Comp. Ex. 2 | HMF | 72.74 | 5.63 | 4.63 |
| Ex. 3 | 85% HMF w/BHA | 78.98 | 1.72 | 0.38 |
| Comp. Ex. 3 | 85% HMF | 54.99 | 2.81 | 2.26 |
| Ex. 4 | 10% HMF w/BHA | 6.66 | 3.24 | 2.64 |
| Comp. Ex. 4 | 10% HMF w/formic | 6.77 | 2.67 | 2.16 |
| Comp. Ex. 5 | 10% HMF | 6.90 | 3.07 | 2.46 |

Examples 6 and 7

These examples were performed to assess whether the antioxidant BHA would also effectively stabilize ester and ether derivatives of HMF, in addition to HMF.

Ester Derivative:

For the ester example, 5-acetoxymethylfurfural (AcHMF) was purchased commercially (from Aldrich) and recrystallized from an n-hexane/methyl tert-butyl ether mixture to improve its purity. To a vial containing 500 ppm equivalent of BHA, 900 mg of AcHMF was added. A second sample containing 700 mg of AcHMF was prepared without BHA for comparison. The headspace was purged with argon and the AcHMF was melted and mixed. The samples were re-exposed to an air atmosphere and placed in an 85° C. dark oven, and analyzed after one week and again after two weeks.

The stabilizer clearly does not have an adverse effect, but at least under the conditions and in the timeframes tested, neither was there any appreciable degradation so that under the recited conditions the results were inconclusive.

TABLE 4

| Description | Week 1 (wt %) | Week 2 (wt %) |
|---|---|---|
| AcHMF - Blank | 94.57 | 94.59 |
| AcHMF - 500 ppm BHA | 94.13 | 94.34 |

The HMF and AcHMF for the ester example were analyzed by ultra-performance liquid chromatography (UPLC), using a Waters Acquity H-Class UPLC apparatus with TUV detector—Monitor at 280 nm, and the following additional analysis details:

Column: Waters BEH C18 2.1×50 mm, 1.7 □m
Temperature: 50° C.
Flow rate: 0.5 mL/min
Purge solvent: 10% Acetonitrile
Wash solvent: 50% Acetonitrile
Solvent C: 50% Acetonitrile
Solvent D: Water
Gradient:

| Time (min) | % C | % D |
|---|---|---|
| initial | 10 | 90 |
| 0.60 | 46 | 54 |
| 0.80 | 99 | 1 |
| 0.96 | 99 | 1 |
| 0.97 | 10 | 90 |
| 2.50 | 10 | 90 |

Injection volume: 0.5 uL
Run time: 2.5 min

Ether Derivative:

For the ether derivative of HMF, 5-butoxymethylfurfural (BMF) was recrystallized from n-hexane until no more butyl levulinate was observable by NMR. BMF (700 mg) was added to a vial containing 500 ppm equivalent of BHA followed by thorough mixing. For comparison, 300 mg of BMF was placed in a vial containing no BHA. The vials were kept in a dark 85° C. oven and sampled for analysis after 1 and 2 week intervals.

The test results were as shown in Table 5:

TABLE 5

| Description | Week 1 (GC % area) | Week 2 (GC % area) |
|---|---|---|
| BMF - Blank | 98.079 | 96.546 |
| BMF - 500 ppm BHA | 99.327 | 98.773 |

The BMF was analyzed by gas chromatography. The sample was diluted to a concentration of 1 mg/mL with acetonitrile and the GC area percent was measured as reported in Table 5. The starting material was >99.9% by GC area. While not all decomposition products were identified and indeed while some degradation products may not have been detected, nevertheless the results demonstrate that BHA was helpful for stabilizing the ether derivative BMF.

Particular details of the analytical method were as follows:

Instrument: Agilent 7890 GC with 7693 autosampler
Column: DB-5 UI 60 m×250×0.25 □m×0.25 □m
Carrier gas: $H_2$
Flow rate: 1 mL/min (constant)
Injector temperature: 200° C.
Split: 50:1
Detector: 340° C.
Temperature program: Initial: 50° C.
Ramp 1: 5°/min to 180° C.
Ramp 2: 20° C./min to 200° C. hold 1 min

What is claimed is:

1. A process for improving the degradation resistance of hydroxymethylfurfural or of a derivative of hydroxymethylfurfural, comprising adding one or more antioxidants to hydroxymethylfurfural or to a derivative of hydroxymethylfurfural.

2. The process according to claim 1, wherein butylated hydroxyanisole is included in the one or more antioxidants.

* * * * *